United States Patent [19]

Dauphinee

[11] Patent Number: 4,656,427

[45] Date of Patent: Apr. 7, 1987

[54] LIQUID CONDUCTIVITY MEASURING CIRCUIT

[76] Inventor: Thomas M. Dauphinee, 36 Avenue Road, Ottawa, Canada, K1S 0N9

[21] Appl. No.: 822,256

[22] Filed: Jan. 24, 1986

[30] Foreign Application Priority Data

Feb. 5, 1985 [CA] Canada .................................. 473595

[51] Int. Cl.$^4$ ............................................. G01N 27/02
[52] U.S. Cl. .................................. 324/444; 324/65 R; 324/443; 204/400
[58] Field of Search ................. 330/110, 9; 73/170 R, 73/170 A; 204/400, DIG. 9; 324/441–450, 64, 65 R

[56] References Cited

U.S. PATENT DOCUMENTS

| | | | |
|---|---|---|---|
| 3,495,164 | 2/1970 | Dauphinee | 324/64 |
| 3,757,205 | 9/1973 | Dauphinee | 324/64 |
| 3,906,353 | 9/1975 | Murdock | 324/442 |
| 4,118,663 | 10/1978 | Barben | 324/443 |
| 4,439,693 | 3/1984 | Lucas | 330/9 |
| 4,511,845 | 4/1985 | Dauphinee | 324/444 |
| 4,527,128 | 7/1985 | Bittner | 330/9 |

FOREIGN PATENT DOCUMENTS 1148002 3/1985 U.S.S.R. .................................. 324/64

Primary Examiner—Reinhard J. Eisenzopf
Assistant Examiner—Jose M. Solis
Attorney, Agent, or Firm—R. William Wray & Associates

[57] ABSTRACT

A liquid conductivity measuring circuit with power-save features is described for use with a four electrode conductivity cell having two potential electrodes and two current electrodes positioned in the cell in spaced relation in a particular sequence with a first operational amplifier having its output connected and its inputs connected via an isolating capacitor and a buffer amplifier and a voltage setting resistance to a source of square-wave voltage, a second operational amplifier having its inputs connected to ground and via an isolating capacitor and its output connected to a reference resistance such as to control the current through the reference resistor to maintain one electrode at a constant potential, readout means being adapted to measure, on initiation of a single or small number of square-wave voltage cycles in a period short enough that no significant change of polarization of the potential electrodes can occur, the voltage between the positive and the negative half cycles or the change from zero to either half cycle of the voltage across the resistor, the measurement being a function of the current through the reference resistor and conductivity cell and therefore a measure of the conductivity of the liquid in or passing through the cell.

6 Claims, 4 Drawing Figures

LIQUID CONDUCTIVITY MEASURING CIRCUIT

BACKGROUND OF THE INVENTION

This invention relates to a low power liquid conductivity measuring circuit for use in an oceanographic probe or portable salinometer.

The salinity of seawater is related to conductivity and it is well known that salinity can be measured in this way. There are various techniques and apparatus for measuring conductivity of seawater by sensing apparatus lowered into the sea on the end of a cable. There is also apparatus available for use at the surface on ships and in land based laboratories for measuring the conductivity of water samples taken in sample bottles by oceanographic survey organization and other groups interested in the salinity distribution of seawater in the various bodies of water throughout the world.

Earlier conductivity measuring circuits are described in U.S. Pat. No. 3,474,330 issued Oct. 21, 1969 to applicant; U.S. Pat. No. 3,495,164 issued Oct. 10, 1970 to applicant; U.S. Pat. No. 3,757,205 issued Sept. 4, 1973 to applicant; and in U.S. Pat. No. 3,963,979 issued June 15, 1976 to applicant. In addition, salinometer conductivity cells and measuring circuitry therefore are described in U.S. patent application Ser. No. 416,013 filed Sept. 8, 1982 now U.S. Pat. No. 4,511,845 issued April 1985 in the names of applicant and Christopher G. M. Kirby.

It is an object of the invention to provide a very low power conductivity circuit having a minimum number and cost of components which can be packaged in small size for use in an oceanographic probe or portable salinometer.

It is a further object of the invention to provide a circuit that can cope with substantial resistances and polarization voltages at the current and potential electrodes of the measuring cell and allow for the fact that the cell is a flowthrough tube open and grounded at both ends to the ocean in the case of the in-situ cell or grounded through unknown impedances at both ends in the case of the salinometer.

It is a further object of the invention to provide a circuit designed to ensure nearly zero dc current in the conductivity cell to prevent generation of gas at the current electrodes and have provisions for at least partial balancing of the circuit so that the smallest significant variation can be easily amplified to easily measured values.

It is a further object of the invention to provide a circuit that will give measurements at frequent intervals and in short periods of time so that other measurements can also be taken while the sensor probe is being traversed through the water, for instance by lowering from a ship.

SUMMARY OF INVENTION

These and other objects of the invention are achieved by a liquid conductivity circuit for use with a four electrode conductivity cell with two potential (P1,P2) and two current electrodes (C1,C2) in the sequence C1P1C2P2 having two modes: a quiescent mode in which the electrode voltages and amplifier outputs are maintained at ground potential so that the only loads on the power supply are the quiescent currents of operational amplifiers and a low power readout device and an active mode in which the voltage between the potential electrodes of the cell is controlled to bear a fixed relation to a driving voltage by supplying current to electrode C1, switch means for holding the circuit normally in the quiescent mode, but periodically switching for a brief period into the active mode, isolation means to ensure that no significant current is drawn from the potential electrodes in the active mode, means to cause the driving voltage, and hence the voltage between the potential leads of the cell, to go through a single (or a small number of) square-wave voltage cycle in a period short enough that no significant change of polarization at the electrodes can occur and means to measure, as a function of the driving voltage, that part of the current passing through the cell which generates the square-wave voltage between the potential electrodes, comprising a reference resistor in series with current electrode C2, circuit means to measure the voltage across the reference resistor, and circuit means to control the current through the reference resistor to maintain the electrode P2 at a constant potential.

BRIEF DESCRIPTION OF DRAWINGS

In drawings which illustrate embodiments of the invention.

DESCRIPTION OF AN EMBODIMENT

The circuits to be described are designed to give readings in conductance units because of the probability of encountering nearly fresh water which has very high resistivity They are based on the fact that operational amplifiers (op amps) are available having very low quiescent-state currents (say 1 ma or less), input currents of the order of 1 na or less, high gain, and low zero offset. Although 1 na would generate excessive polarization at the potential electrodes over time, the rate of change of polarization is such that changes over the few milli-seconds that are permitted for an ocean measurement can be neglected.

Figure 1:
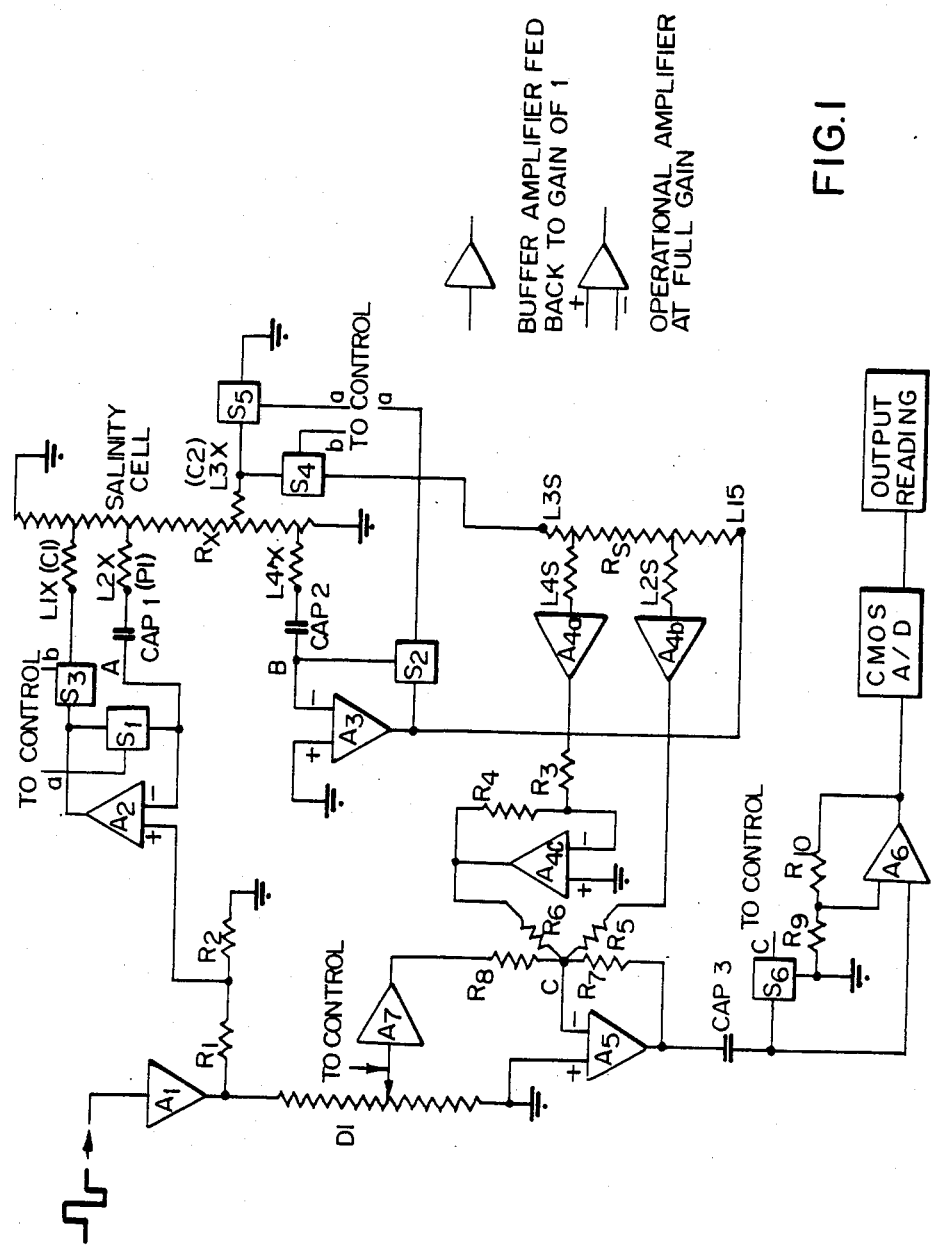
FIG. 1 is a schematic diagram according to the invention.

Referring to FIG. 1, a conductivity measuring salinity cell shown schematically as Rx has current electrodes C1 and C2 and potential electrodes P1 and P2 connected via lines L1x, L3x, L2x, and L4x respectively to the measuring circuitry. Salinity cells are known devices and typical examples of the design of these are shown in U.S. Pat. No. 3,963,979 and in U.S. patent application Ser. No. 416,013.

The whole circuit is held in the quiescent mode with zero drive signal and zero current in all leads of the conductivity cell. The potential leads are ac grounded but isolated by capacitors CAP1, and CAP2 and the current leads can be either open circuit or held at ground potential as shown, preferably the latter. When a reading is required the circuit is first switched from the quiescent mode to the active mode via CMOS switches (S1,S2, S3, S4, S5, and S6) but still with zero drive voltage and hence with zero current in the cell. A single cycle (or small number of cycles) of square wave drive voltage is then applied to the input of buffer amplifier A1 and attenuated to an appropriate level $+-Vr$ by potential divider R1 and R2 and presented to the current drive op amp A2 resulting in a current passing through the cell to generate an exactly compensating square wave voltage between the cell potential electrodes P1 and P2. This current which is a function of the conductivity of the water also passes through a reference resistor Rs in series with the cell. In the quiescent period, switches S1 and S2 are closed and S3 and S4 are open ensuring that points A and B are held at ground potential by op amps A2 and A3 respectively and that there is no current in the current leads L1x and L3x. The output and suppression amplifiers (A4a, A4b, A4c, A5,A6,A7) will also be quiescent and at zero output. Optionally switches S3 and S4 may be omitted and the cell current leads held at ground potential by amplifiers A2 and A3. This is preferable to avoid ac pickup and necessary if the sample water is not otherwise connected to ground. A switch S5 to connect cell lead L3x and line L3s to ground directly is also useful to ensure that no cell electrode discharge current passes through the series reference resistor Rs.

Just before the onset of the square wave drive pulse, switches S1, S2, and S5 are opened and switches S3,S4 (if present) closed, freeing points A and B to follow potential changes at the potential leads L2x and L4x without drawing current. This allows op amps A2 and A3 to control the voltages of points A and B to the values $+-Vr$ and 0 respectively. Current will pass through the sample cell Rx and reference resistor Rs in the amount required to generate the voltage $+-Vr$ between points A and B no matter what the level of polarization at the corresponding electrodes may be. This will happen even with changing polarization voltages and/or lead resistances in series with the current electrodes L1x and L3x. The current through the cell required to maintain point B at 0 v when point A is at $+-Vr$ is therefore proportional to the cell conductance. This current is measured from the voltage across the reference resistor Rs, using a high-impedance differential amplifier circuit made up of buffer amplifiers A4a and A4b op amp A4c, and resistors R3,R4,R5 and R6 to prevent shunting of the measuring current and an inverting op amp A5 which holds point C at ground potential by feedback through resistor R7. If desired a suppression current supplied from a digitally-controlled divider network D1 and one or more amplifiers A7 and resistors R8 can be fed to point C to reduce the output of amplifier A5 and/or allow greater gain. Capacitor CAP3 and switch S6 (which is closed only in the quiescent periods) ensure that any residual zero offset in the amplifiers and switches is eliminated. The magnitude of the current change between the positive and negative half cycles, or the change from zero to either half cycle, as measured from the change of the voltage across the resistor Rs may be used to measure cell conductances. The preferred method to read the unbalance is to take separate readings of the output CMOS A/D, after amplification to an appropriate level by A6 for the $+$ and $-$ half cycles of the square wave drive pulse and subtract the two readings electronically or in a subsequent computation to obtain the final answer. This prevents any slight offset which might occur on switching from the quiescent to the active mode from creating an error. Alternatively, switch S6 can be left closed for a short period in the active mode to eliminate the offset before the square-wave current cycle is initiated. After a reading, the complete circuit is then returned to its quiescent state with the complete cycle being completed before polarization or zero offset changes in the amplifiers have time to generate measurable errors in the measurement. Any slight buildup of offsets is removed in the following quiescent period.

A great advantage of this circuit is that in the quiescent mode the total current can be of the order of a few ma or less at $+-6$ v, including a CMOS A/D converter on standby or several parallel suppression networks to give finer subdivision of the suppression scale. Relatively high impedances are allowed in the loads of all amplifiers, except A2 and A3 which are in series with the cell, so that with a cell voltage of for example 0.2 to 1 v the pulse current drain in a 250 r cell during approximately 0.02 s of reading time will be less than 5 ma, and the average power drain from the batteries of the order of 25–100 mw at 5–10 readings per second. This power is easily supplied by, say, two 6 v alkaline lantern batteries for long periods of time. For lesser accuracies, say to $+-0.01$ in salinity which only requires measurement of conductivity ratio to about 1/4000 of the conductivity at S=35, zero offsets may be low enough at the outputs that CAP3 and S6 can be dispensed with and the A/D converter connected directly to the output of A5. With appropriate switching the A/D converter can be used in common for all circuits in the system. Reversal of the current and measurement of the resultant change effectively doubles the sensitivity and gets rid of residual zero offsets at the same time, but requires two readings, before and after the reversal. The same doubling of sensitivity and elimination of zero error can also be obtained by grounding CAP3 through S6 only during the 1st half cycle (allowing a short wait period after the voltage is applied to ensure equilibrium is achieved) and then reading the A/D during the second half cycle. However its chief function is to prevent gassing and excessive dc bias at the current electrodes.

Figure 2:
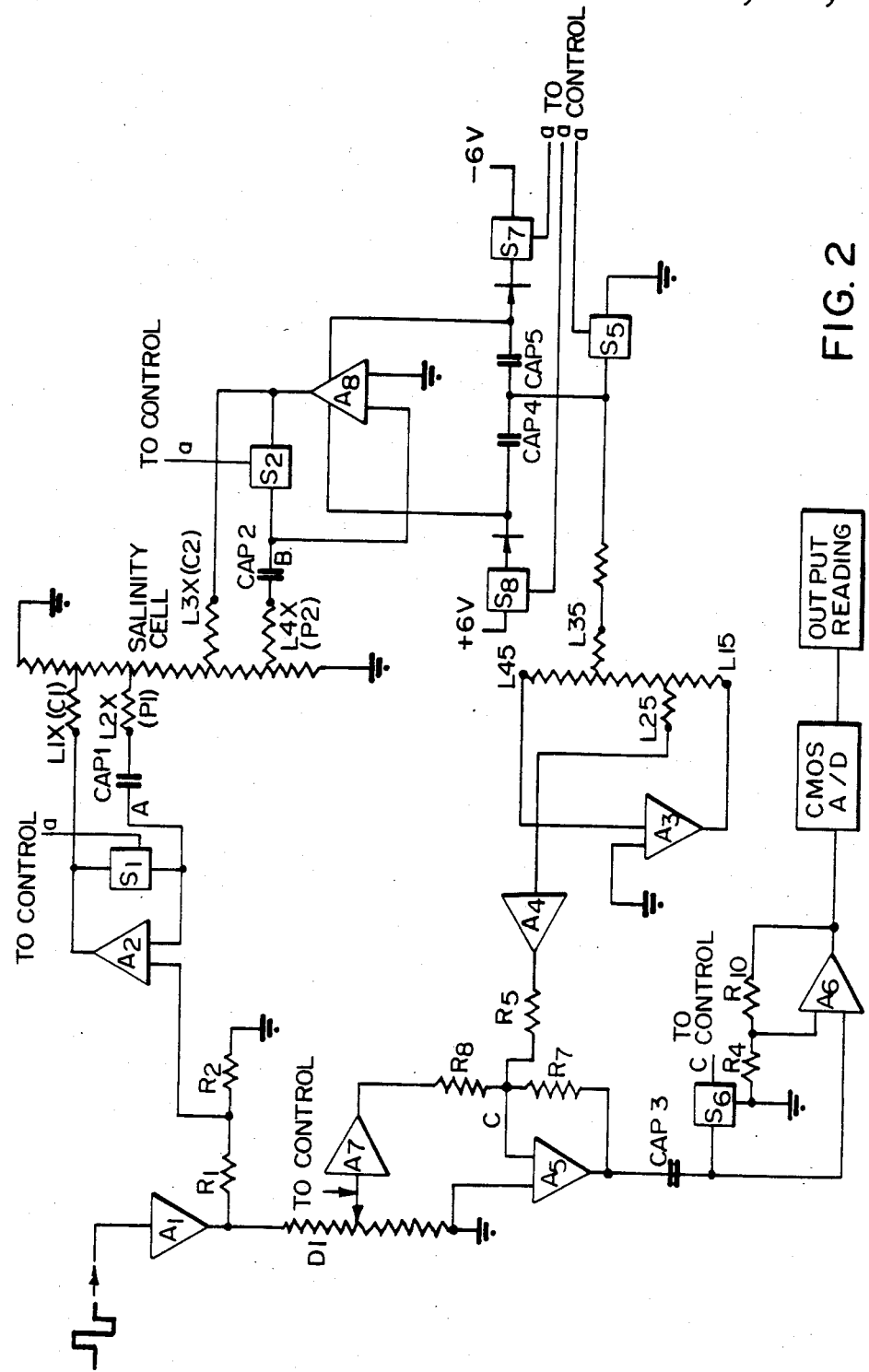
FIG. 2 is a diagram of similar circuitry designed to avoid the use of a differential amplifier.

Use of a differential amplifier (as shown in FIG. 1), which must have accurately matched resistance ratios, can be avoided by using an isolated power supply and amplifier, as shown in FIG. 2. In the quiescent period switch S5 connects the common point of the storage capacitors CAP4 and CAP5 (and L3s) to ground, while switches S7,S8 connect current electrodes, C1, C2 to $+-6$ v power supplies, thus simultaneously holding one end of the cell at ground potential and ensuring that the capacitors are charged. Opening switches S5,S7,S8 during the active cycle gives an isolated supply from which amplifier A8 draws current to hold the inner potential lead of the sample cell at ground potential, while at the same time ensuring that all of the measuring current passes through Rs. Since amplifier A3, which supplies the cell current through Rs, does so in such a way as to control the inner potential lead L4s of the reference resistor to ground potential the voltage at the outer potential leads L2s is therefore exactly proportional to the cell current, and hence to the conductance of the cell.

It should be noted that because the sequence of four electrodes along the conductance cell alternates between current and potential electrodes (C1,P1,C2,P2) as shown there is no ac shunt current past P2 because P2 is always held at zero potential. Also, since the cell current required to generate the voltage $+-Vr$ is measured in series with C2, the fact that some of the current supplied by amplifier A2 may represent shunt current passing out of the other end of the cell has no effect on the measurement.

Figure 3:
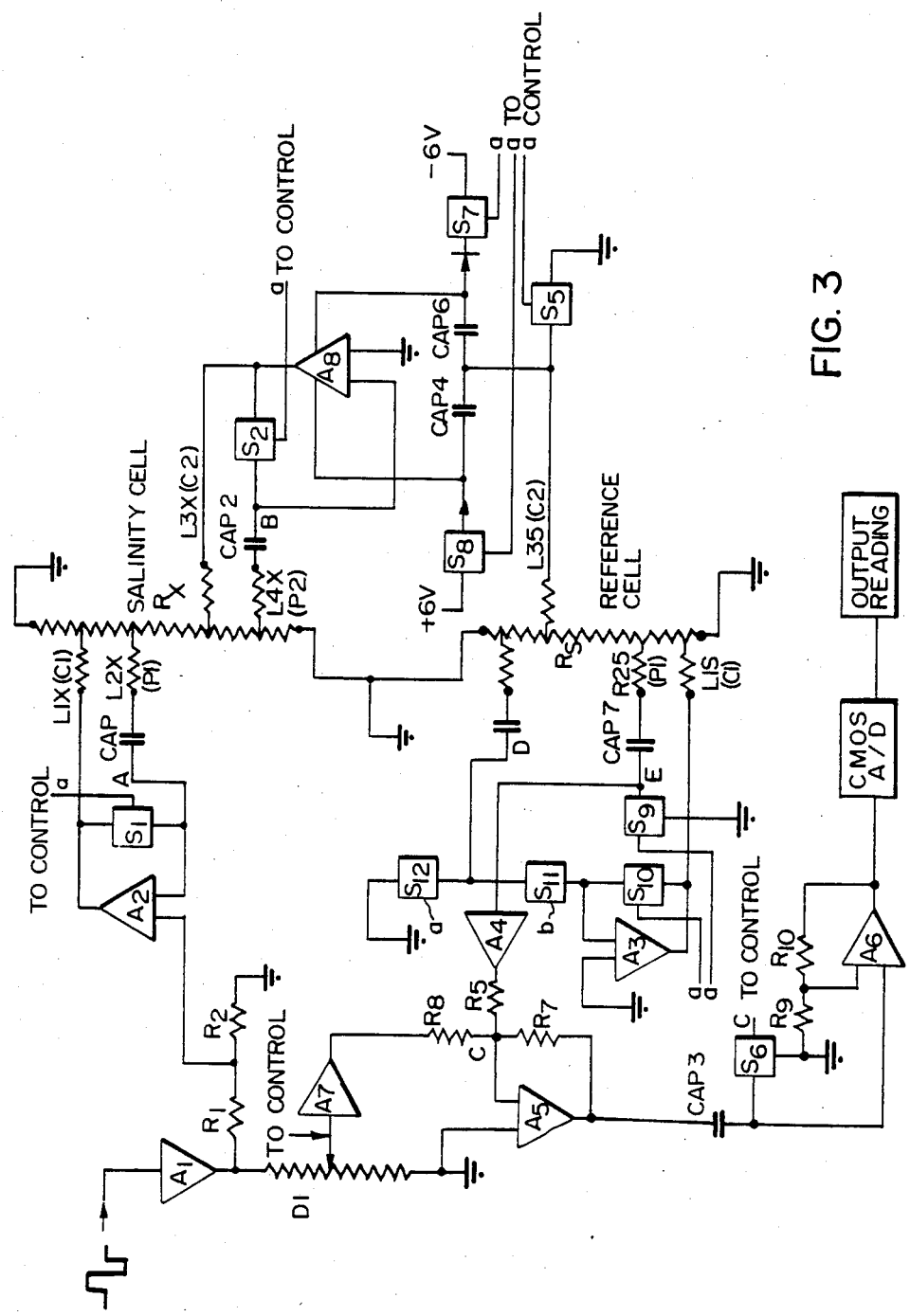
FIG. 3 is a diagram of similar circuitry designed for measurement of the ratio of conductances of two cells.

The circuit of FIG. 3 shows a very effective way of measuring the ratio of conductances of two cells, both of which have some electrical contact with the surroundings. This is required for a salinometer in which the variation of conductivity of standard seawater in a second cell (at the same temperature as the sample because both cells with temperature equalizing means are immersed in the same stirred bath) is used to compensate for temperature variations and avoid thermostatting, or complicated temperature compensation circuits which are only approximations of the correct values. For the ratio measurement the standard cell with blocking capacitors CAP6 and CAP7 in the potential leads L4s and L2s to prevent lead currents, and switches S9, S10, S11, S12 to bring the appropriate points to ground potential in the quiescent mode is put in place of the resistor Rs of FIG. 2 and the isolated power supply is used as before to allow the inner potential leads of both cells to be maintained at ground potential. This eliminates shunt current to the heat exchangers from either cell and therefore effectively puts the two cells in series. The voltage at the outer potential lead of the standard cell Rs is then proportional to the ratio Rt=Csample/Cstandard, as required by the equations of the Practical Salinity Scale 1978. This is taken from the leads via capacitors CAP6 and CAP7 (across D to E) to amplifier A4 as before. Switches S9 and S10 are used in a similar fashion to S1 and S2.

Rt, the ratio of conductivities Cx,C35 of unknown and standard (s) seawater with conductivity ratio=1 (S=35.00000) as required by the IPTS equations, is derived as follows:

The same current passes through the two cells, consequently $$Vx \times Cx \times Kx = Ix = Is = Vs \times Cs \times Ks$$

where Vx,Vs are the voltages across the cells, Kx,Ks are their cell constants as determined by their dimensions, and Cx,Cs are the conductivities of the unknown and standard seawaters. In this case Vx, Kx and Ks are constants. Therefore $$Cx/Cs = (Vs \times Ks)/(Vx \times Kx) = Vs \times K$$

where K is a constant.
If the same water is now put in both cells $$Cx/Cs = 1 = Vs^* \times K, \text{ therefore } K = 1/Vs^*$$

If unknown (x) water is now put in the x cell and standard seawater of known conductivity ratio Rs in the s cell, then the conductivity ratio (Rxs) of unknown to this standard water is $$Rxs = Cx/Cs = Vs(xs) \times K = Vs(xs)/Vs^*$$

and the conductivity ratio Rt=Cx/C35 is $$Rt = Rxs \times Rs$$

Figure 4:
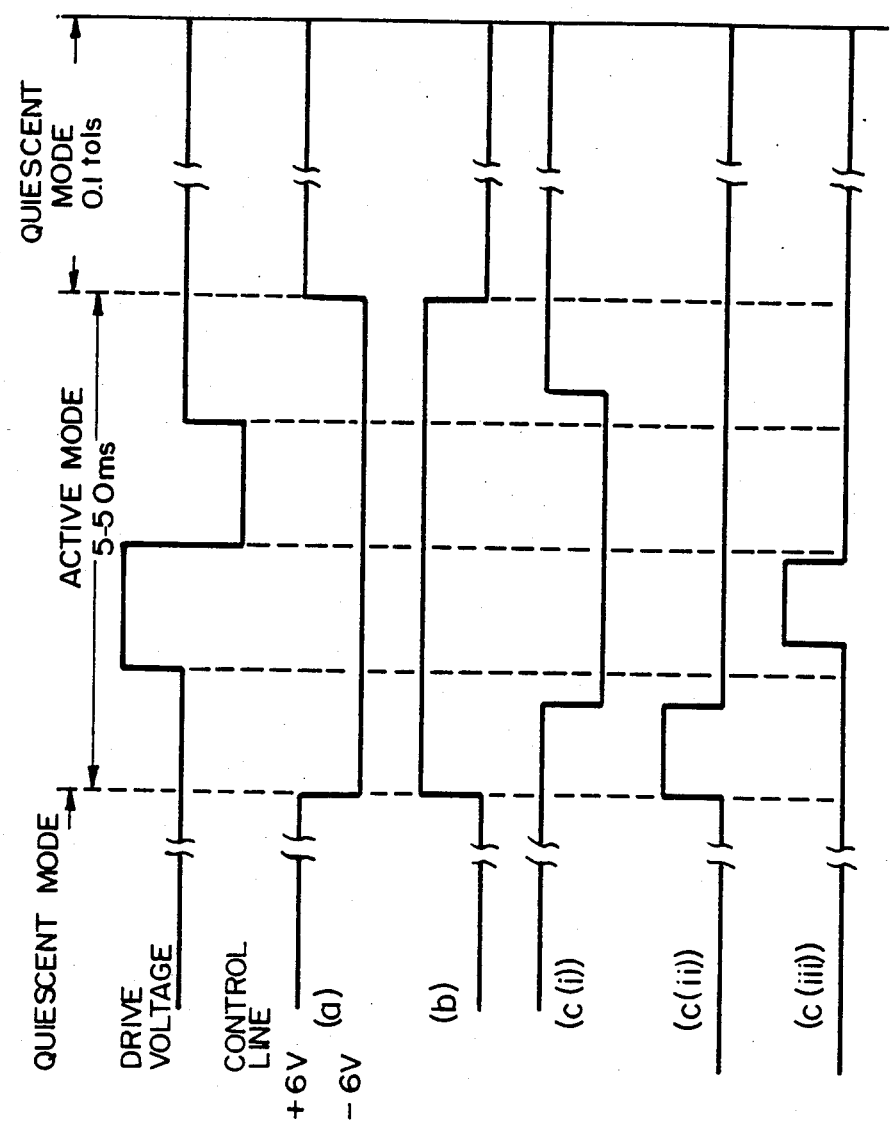
FIG. 4 is a timing diagram of the control lines to the switches.

The preferred switches at this time are CMOS types 4066 quad bilateral switches, which have negligible power drain, very high OFF resistance and quite low ON resistance. The control line for each section is +ON and −OFF. The timing of the switches is as follows: S1, S2, S5, S7, S8, S9, S10, S12 are ON in the quiescent mode and OFF in the active mode (control line (a)); S11 (and S3, S4 (if present) is ON in the active mode (before and through the pulse) and OFF in the quiescent mode (control line (b)); S6 (control line (c)) is either (i) ON in quiescent mode and active mode before the square-wave pulse or (ii) ON in the active mode before the pulse only, or (iii) delayed ON in the first half cycle of the pulse only, depending on the choice of output reading system, as described earlier. In the quiescent mode the drive voltage is zero, in the active mode it is zero for a short period then goes through one complete square wave voltage cycle and returns to zero. A timing diagram of the control lines is shown in FIG. 4.

It will be readily apparent to a person skilled in the art that a number of variations and modifications can be made without departing from the true spirit of the invention which will now be pointed out in the appended claims.

I claim:
1. A liquid conductivity measuring circuit for use a four electrode conductivity cell having two potential electrodes (P1 and P2) and two current electrodes (C1 and C2) positioned in the cell in spaced relation in the sequence (C1, P1,C2,P2) comprising:
   (a) a first operational amplifier having its output connected to C1 and its inputs connected via an isolating capacitor to P1 and via a buffer amplifier and a voltage setting resistance to a source of square-wave voltage,
   (b) a first switch connected across the first operational amplifier between its output and noninverting input,
   (c) a reference resistance connected at one end to current electrode C2 and having current and potential tapping points,
   (d) a second operational amplifier having its inputs connected to ground and via an isolating capacitor to P2 and its output connected to the reference resistance such as to control the current through the reference resistor to maintain electrode P2 at a constant potential,
   (e) a second switch connected across the second operational amplifier between its output and non-inverting input,
   (f) readout means for measuring the voltage across appropriate points of the reference resistor,
   (g) said first and second switches when closed defining a quiescent mode of operation in which the electrode voltages and amplifier outputs are maintained at ground potential so that the only loads on the power supply are the quiescent currents of the operational amplifiers and the readout means and when open, an active mode in which the voltage between the potential electrodes of the cell is controlled by the first operational amplifier to bear a fixed relation to a square-wave driving voltage by supplying current to electrode C1,
   (h) said readout means adapted to measure, on initiation of a single or small number of square-wave voltage cycles in a period short enough that no significant change of polarization of the potential electrodes can occur, the voltage between the positive and the negative half cycles or the change from zero to either half cycle of the voltage across the resistor, said measurement being a function of the current through the reference resistor and conductivity cell and therefore a measure of the conductivity of the liquid in or passing through the cell.
2. A liquid conductivity measuring circuit as in claim 1 wherein the reference resistor is a second conductivity cell similar in construction and operation to the conductivity cell with the readout means connected to the potential electrodes of the second conductivity cell such as to measure the voltage thereon and thus the ratio of the conductivity of the liquids in or passing through the two cells.

3. A liquid conductivity measuring circuit as in claim 1 wherein the readout means is a differential amplifier and a resistance bridge network connected via buffer amplifiers to the reference resistor and giving an output via an inverter amplifier to output reading means.

4. A liquid conductivity measuring circuit as in claim 3 further comprising suppression means made up of an amplifier connected via a settable voltage divider to the source of square-wave voltage drive input and to the output of the differential amplifier and the input of the inverter such as to provide appropriate levels of voltage to the output reading means.

5. A liquid conductivity measuring circuit as in claim 1 wherein a third operational amplifier having an isolated power supply adapted to be recharged as required during the quiescent period is connected between the conductivity cell and the reference resistor such as to maintain P2 at ground potential while the second operational amplifier connected to the reference resistor or second conductivity cell maintains the inner potential point or electrode of the reference cell or resistor at ground potential and the readout means is connected to the outer potential point or electrode such as to measure the voltage thereon.

6. A liquid conductivity measuring circuit as in claim 2 wherein a third operational amplifier having an isolated power supply adapted to be recharged as required during the quiescent period is connected between the conductivity cell and the reference resistor such as to maintain P2 at ground potential while the second operational amplifier connected to the reference resistor or second conductivity cell maintains the inner potential point or electrode of the reference cell or resistor at ground potential and the readout means is connected to the outer potential point or electrode such as to measure the voltage thereon.

* * * * *